(12) United States Patent
Brown et al.

(10) Patent No.: US 10,688,069 B2
(45) Date of Patent: Jun. 23, 2020

(54) SPORTS HEALTH PERFORMANCE COMPOSITION

(71) Applicant: REV Pharmaceuticals LLC, Jackson, WY (US)

(72) Inventors: Beth Anne-Szkudlarek Brown, Jackson, WY (US); Anthony Lemus, Jackson, WY (US); Marnie L. Peterson, Jackson, WY (US)

(73) Assignee: REV Pharmaceuticals LLC, Jackson, WY (US)

( * ) Notice: Subject to any disclaimer, the term of this patent is extended or adjusted under 35 U.S.C. 154(b) by 0 days.

(21) Appl. No.: 15/474,375

(22) Filed: Mar. 30, 2017

(65) Prior Publication Data

US 2017/0281581 A1    Oct. 5, 2017

Related U.S. Application Data

(60) Provisional application No. 62/315,859, filed on Mar. 31, 2016.

(51) Int. Cl.
| | |
|---|---|
| *A61K 31/198* | (2006.01) |
| *A61K 31/352* | (2006.01) |
| *A61K 9/00* | (2006.01) |
| *A61K 9/107* | (2006.01) |
| *A61K 47/18* | (2017.01) |
| *A61K 45/06* | (2006.01) |
| *A61N 1/36* | (2006.01) |

(52) U.S. Cl.
CPC .......... *A61K 31/198* (2013.01); *A61K 9/0014* (2013.01); *A61K 9/107* (2013.01); *A61K 31/352* (2013.01); *A61K 45/06* (2013.01); *A61K 47/183* (2013.01); *A61N 1/36* (2013.01)

(58) Field of Classification Search
None
See application file for complete search history.

(56) References Cited

U.S. PATENT DOCUMENTS

| | | | | |
|---|---|---|---|---|
| 5,595,753 A | * | 1/1997 | Hechtman | A61K 31/198 424/434 |
| 5,922,332 A | * | 7/1999 | Fossel | A61K 8/0208 424/401 |
| 6,444,234 B1 | * | 9/2002 | Kirby | A61K 9/0014 424/449 |
| 7,629,384 B2 | | 12/2009 | Fossel | |

FOREIGN PATENT DOCUMENTS

EP        1732577       *    4/2013

OTHER PUBLICATIONS

Moghadam et al. (AAPS J. Mar. 2008; 10(1): 120).*
Sapra et al. (AAPS J. Mar. 2008; 10(1): 120).*
Setty et al., (2010) "Effect of Essential Oils as Penetration Enhancers on Percutaneous Penetration of Furosemide Through Human Cadaver Skin," Acta Pharmaceutica Sciencia, 52: 159-168.
Fox et al., (2011) "Transdermal Drug Delivery Enhancement by Compounds of Natural Origin," Molecules, 16: 10507-10540.
Hyldahl et al., (2010) "Effects of Ibuprofen Topical Gel on Muscle Soreness," Medicine & Science in Sports & Exercise, pp. 614-621.

* cited by examiner

*Primary Examiner* — Bong-Sook Baek
(74) *Attorney, Agent, or Firm* — Kagan Binder PLLC

(57) ABSTRACT

A topical composition that includes L-arginine that is used as a sports health composition. The composition can further include forskolin. Disclosed is a method of using the topical composition.

7 Claims, No Drawings

SPORTS HEALTH PERFORMANCE COMPOSITION

CROSS-REFERENCE TO RELATED APPLICATION & PRIORITY CLAIM

This application claims the benefit of U.S. Provisional Application No. 62/315,859, filed Mar. 31, 2016, which is incorporated by reference in its entirety herein.

BACKGROUND

Athletes work hard to prepare and perform successfully throughout a competitive season or for major events. Unfortunately, many ignore or forget the performance benefits gained through including recovery strategies within their daily training programs. Indeed there is a tendency for many athletes to limit the use of recovery techniques to times when they are ill or injured. Yet recovery strategies have far more benefits for athletes than merely as tools to assist with rehabilitation or recuperation.

Recovery is one of the basic principles of training methodology (Rushall & Pyke, 1990) and it has two primary roles: The first concerns monitoring the athlete's adaptation to training and stress so that appropriate recovery strategies can be determined. The second relates to the selection of specific recovery techniques and strategies to minimize any residual fatigue from training and competing.

The responsible athlete will also monitor training adaptations through regular recordings in a training diary or log book. Maintaining a daily record is an essential training tool for all athletes as it enables them to learn how to evaluate their stress levels and their adaptive responses. Learning to recognize "how they feel" is one of the most important skills any athlete can acquire. Recordings of the quality of sleep, morning rest rate and morning body weight, and a daily rating of fatigue levels are four critical markers that should be recorded regularly by athletes.

Recovery Strategies: Management

There are four generic types of training and competition fatigue (Calder, 2003). There are Metabolic Fatigue (energy stores); Neural Fatigue of either or both the peripheral nervous system (localized force production) and central nervous system (drive/motivation) Psychological Fatigue (emotional and social stress factors); and Environmental Fatigue (climate and travel).

A good coach understands not only what is being stimulated through prescribed training sessions, but also what is being fatigued. The challenge is to recognize the type of fatigue and then select specific strategies to reduce and minimize this fatigue as soon as possible after the training or performance situation. There are three major specialty areas to include when designing appropriate recovery strategies for an athlete's training program.

Nutrition: Fluid and Fuel for Recovery

The most important nutritional consideration for recovery relate to fluid and fuel replacement strategies (Burke, 2000). Monitoring fluid loss so that it is kept to a minimum is essential. A bodyweight loss of two percent or more during exercise will result in a reduction in aerobic output. If an athlete becomes excessively dehydrated, not only can this be dangerous and lead to overheating their aerobic capacity can be reduced by up to six-percent.

Adequate supplies of glycogen in the muscle and in the liver are needed to support the energy demands and promote recovery for the next training session. Athletes can minimize the effects of metabolic fatigue by starting each session with their fuel tanks full. They can top-up during the event with sports drinks and take other carbohydrate and protein foods. Small amounts of protein taken with carbohydrates before, during, and after hard training, are also recommended to help minimize muscle protein breakdown as a result of heavy workloads (Tarnopolsky, 2000).

Nutritional supplements should be used with caution and sound scientific advice. Many coaches and athletes are pressured to use supplements and new products and it is often difficult to source reliable evidence-based information about what is appropriate and safe to use. A useful website for advice on this area is www.ais.org.au/nutrition Physical Therapies A wide variety of activities and therapies are used to assist with recovery from training fatigue. Unfortunately, many recovery techniques popular with athletes and coaches have not been extensively investigated by scientists so coaches and athletes often rely on anecdotal information about what is best to use. The following list is an indication of some of the most commonly used recovery techniques.

Rest: Passive Rest

Passive rest, particularly in the form of sleep, is an area that is not well understood by either coaches or athletes. Sleep is probably the most important form of recovery an athlete can have. A good night's sleep of seven to nine hours provides invaluable adaptation time for adult individuals to adjust to the physical, neurological, immunological and emotional stressors that they experience during the day. An adolescent experiencing heavy training and a growth spurt may need up to ten hours a night and athletes who are sick often need more sleep as a part of recuperation. However, too much sleep can be detrimental to performance as it can slow down the central nervous system and lead to increased levels of melatonin that can leave the athlete feeling slow and lethargic.

Rest: Active Rest

Active rest is much undervalued by athletes. The end of the loading component of the training session is an ideal time to introduce active recovery activities, although active rest strategies can also be interspersed easily throughout the session (i.e., sets and reps). Activities can be selected to fulfill several tasks. They can either help to recover the physiological state of the athlete (light jog, walk, swim or cycle to recover the lactate system), recover neural fatigue (light jostling/shaking of muscle groups), or used as a means of psychological and emotional restoration (light but different activities).

Cross-training can also be used as a form of active rest provided the work intensities are modest (light aerobic) and the exercise undertaken are different to those normally performed in training, e.g., pool work after a game. Rest days are essential. Ideally at least one day per week should be a non-training day. This allows time for physical and psychological recovery as well as time for other interests and personal and family relationships.

Hydrotherapies

A wide range of hydrotherapies have been in use restoratively for several thousand years. Spas, pools, steam rooms, cold pools, and contrast temperature protocols were used by the ancient Greeks and Romans.

One of the few published articles on the effectiveness of hydrotherapies comes from research with nationally ranked Finnish track and field athletes (Vitasalo et al., 1995). Researchers demonstrated that underwater massaging (using the jets in a spa) following plyometrics training helped athletes to maintain leg-explosiveness on the following day.

In contrast, passive rest after such training resulted in a significant reduction in leg power.

The protocols used by the Finnish researchers were very similar to those used by the ancient Romans. Essentially, this routine involves first having a shower, followed by a spa (39 to 40° C.) for three minutes and then a cold shower or a plunge into a cold pool (10 to 15° C.) for 30 to 60 seconds. Warm immersion produces vasodilation of the peripheral circulation and the cold immersion encourages vasoconstriction. Three to five sets of this protocol producing rapid vasodilation and vasoconstriction will accelerate blood flow.

A contrast temperature following the same protocol as outlined above, was used by researchers from the University of Canberra in 1996 to measure lactate recovery in high-performance hockey players after a series of Wingate tests (Sanders, 1996). Results indicated that lactate levels were recovered equally fast by using either the contrast water immersion protocol or the active recovery protocol. Lactate recovery following passive rest was significantly slower.

Showering within five to ten minutes at the end of a training session is a good way to accelerate recovery of both lactates and peripheral neural fatigue. Contrasting temperatures can be achieved with a shower and bath at home or the use of a small paddling pool or tub for cold immersion.

Sports Massage

Many claims are made about the benefits of sports massage and numerous research studies examining these claims have been undertaken over the last 15-20 years. Despite this there is not much evidence-based science to substantiate many claims that are made about the benefits of massage (Calder, 1990). What little information that does exist provides evidence for increased muscle and skin temperatures, leads to a relaxation response as demonstrated by a reduction in resting heart rates, blood pressure and a decrease in excitability of the motor-neuron pool. Improved mood states and feelings of well-being have been recorded in several studies and many athletes will use massage as both a means of relaxing physically and psychologically.

Acupuncture and Acupressure

Acupressure is often performed as an adjunct to sports massage but acupuncture requires more extensive qualifications and is less accessible and more expensive than massage. Both acupressure and acupuncture focus on applying pressure or stimulus to specific points located on 14 meridians (line patterns) on the body. http://smscsqlx.sasktelwebhosting.com/services/exphys/recoverystrategies.pdf The products outlined in this application fit the unmet need for aids to improve "active rest" performance as well as actual performance during the sports activity.

SUMMARY

The present disclosure is generally directed to a product of a nitrous oxide (NO) donor that may be used to enhance both women's and/or men's sports health performance and active rest recovery. In one aspect of the invention is disclosed a topical composition comprising an effective amount of L-arginine with a base or carrier component and skin penetration enhancer, the composition capable of dilating blood vessels to thereby allow lactic acid to dissipate from muscular tissue during exercise or during the recovery phase after exercise.

In other aspects of the invention is disclosed a topical composition comprising an effective amount of L-arginine and forskolin with a base or carrier component and skin penetration enhancer, the composition capable of dilating blood vessels to thereby allow lactic acid to dissipate from muscular tissue during exercise or during the recovery phase after exercise.

In other aspects of the invention is disclosed a topical composition consisting essentially of an effective amount of L-arginine with or without forskolin with a base or carrier component and skin penetration enhancer, the composition capable of dilating blood vessels to thereby allow lactic acid to dissipate from muscular tissue during exercise or during the recovery phase after exercise.

In still other aspects is disclosed a topical composition consisting of an effective amount of L-arginine with a base or carrier component and skin penetration enhancer, the composition capable of dilating blood vessels to thereby allow lactic acid to dissipate from muscular tissue during exercise or during the recovery phase after exercise.

Also disclose is a method for dilating blood vessels to thereby allow lactic acid to dissipate from muscular tissue during exercise or during the recovery phase after exercise comprising delivering a topical composition to an area of the skin where desired, the topical composition comprising an effective amount of L-arginine with or without forskolin, with a base or carrier component and skin penetration enhancer.

DETAILED DESCRIPTION

The present disclosure is generally directed to a product of a nitrous oxide (NO) donor that may be used to enhance both women's and/or men's sports health performance and active rest recovery. An exemplary nitrous oxide donor can include L-arginine, which acts by keeping blood vessels dilated. The dilated blood vessels allow lactic acid to dissipate from muscular tissue during exercise or during the recovery phase after exercise. L-arginine also has several roles in the body such as assisting in wound healing, ensuring that cells divide properly, helping to remove ammonium from the body, facilitating immune function, and promoting the secretion of several hormones including glucagon, insulin, and growth hormone (The Natural Pharmacy, 1998.

Forskolin is a naturally occurring alkaloid derived from the Indian herb *Coleus forskohlii* that has been shown to induce smooth muscle relaxation and increase blood flow. Forskolin binds directly and stimulates adenylate cyclase increasing cAMP concentrations, and can directly reduce intracellular calcium concentrations in smooth muscle causing relaxation in a NO-independent pathway. Forskolin can optionally be used in compositions with L-arginine to enhance dissipation of lactic, thereby increasing sport performance via a NO independent pathway.

L-arginine may be provided as a free base, as L-arginine hydrochloride or as L-arginine alkyl (ethyl, methyl propyl, isopropyl butyl, isobutyl,) esters of L-arginine and salts thereof. Pharmaceutically acceptable salts include hydrochloride, glutamate, butyrate and glycolate.

Administration of L-arginine by intravenous infusion (IV) or orally at doses (6 to 30 gm) induced peripheral vasodilation in humans and improved endothelium-dependent vasodilation, resulting in improved muscle blood flow.

L-arginine oral (12 capsules of 0.5 gm of L-arginine HCL) was administered Bioavailability was 50 to 87% with a time to Cmax of 40 to 60 min Mean Cmax: 6223 and 822 umol/L for 30 and 6 gm IV, and 310+/−152 umol/L for 6 gm oral Half life 60 (IV) to 90 (PO) min No significant changes in hemodynamics at 6 gm doses; blood pressure and total peripheral resistance were significantly decreased after 30 gm IV Increased urinary cGMP and nitrate excretion (correlate with plasma concentrations) with 6 gm and 30 gm IV causing significant increases.

Numerous over the counter products (gels and creams) are available with or without other agents such as ginseng, niacin and L-citrulline (concentrations up to 5%). Since an oral dose of 10 gm of L-arginine produces a peak arginine plasma concentration of 200 to 300 uM and the Km of NOS activity for endothelial cells is approximately 30 to 40 uM, a 10 gm oral dose produces plasma concentrations that are 10-fold above the Km. Therefore, topical administration of L-arginine needs to be delivered at concentrations greater than about 30 to 40 uM to achieve the desired physiological effects. Suitable topical formulations should deliver at least about 50 to 70 mg/L (50 to 70 ug/ml) to the endothelial cell membrane to achieve desired effective amounts of arginine free base. One skilled in the art would readily determine suitable amounts to be delivered in formulations comprising L-arginine hydrochloride or L-arginine alkyl (ethyl, methyl propyl, isopropyl butyl, isobutyl,) esters of L-arginine and salts thereof. In some embodiments, the L-arginine includes about 5 wt % to 60 wt %, about 15 wt % to 50 wt %, or about 20 wt % to 40 wt % of the total weigh of the topical composition.

In some embodiments, the composition can further include forskolin from about 0.01 to about 1 wt %, about 0.1 to about 0.5 wt %, or about 0.1 wt % based on the weight of the topical composition.

Base Components

The L-arginine is included with base or carrier components. The base components include glycols (e.g. propylene glycol USP, polyethylene glycol), oil-in water emulsions, water-in oil emulsions, lipophilic foams, water, anhydrous silicone base, lipophilic foam base, transdermal cream base and mineral oils. In some embodiments, the base component is from about 30 wt % to 80 wt %, about 40 wt % to 70 wt %, or about 50 wt % to 60 wt % based on the total weight of the topical composition. In some embodiments, the base components include base selected from oil in water emulsion, water in oil emulsion, anhydrous silicone base, lipophilic foam base, transdermal cream base, or transdermal gel base.

Those skilled in the art would readily understand how to prepare suitable topical compositions that are formulated with a transdermal cream base. A typical cream base may include commercially available components such as, for example, purified water, humectants, oil in water emulsifiers, lubricants, silicones, rheology enhancers, preservatives, vitamin E and liposomes.

Those skilled in the art would also readily understand how to prepare suitable topical compositions that are formulated with a transdermal gel base. A typical gel base may include commercially available components such as, for example, purified water, alcohols (benzyl alcohol, isopropyl alcohol, ethanol), nonionic and amphiphilic surfactants, emulsifiers cellulose ethers and cellulose derivatives, polyacrylate/polyalkenyl polyether derivatives, and pH adjusters (hydrochloric acid, sodium hydroxide).

Skin Penetration Enhancers

In some embodiments, the disclosed composition is delivered topically to the skin. Unfortunately, dermal and transdermal delivery can be limited by the permeability of the substance or composition. To enhance or improve the absorption or delivery of L-arginine through the skin, skin penetration enhancers may be included. Both chemical and/or physical approaches can be used to enhance the penetration of substances across the skin. A skin penetration enhancer may include compounds that assist in the effective delivery of a desired ingredient (e.g. L-arginine) into the skin. Exemplary skin penetration enhances include volatile oils (e.g. essential oils), fixed oils (e.g. fatty acids) and polysaccharides. Essential oils are volatile, odoriferous substances found in the flowers, fruit, leaves and roots of certain plants. Fatty acids, on the other hand, are composed of aliphatic hydrocarbon chains, which can be either saturated or unsaturated, and include a terminal carboxyl group.

Essential oils are a complex mixture of many diverse and unique chemical compounds. Essential oils can include compounds classified as:

nitrogen- and sulphur-containing compounds (e.g., allyl isothiocyanate found in mustard oil);

aromatic compounds, which are benzene derivatives (e.g., eugenol which is the main constituent of clove oil);

terpenes (e.g., 1,8-cineole in eucalyptus oil) and terpenoids; and miscellaneous compounds (includes long-chain unbranched substances).

Exemplary essential oils include niaouli oil, eucalyptus oil, alpinia oxyphylla oil, turpentine oil, sweet basil and tulsi oil, cardamom oil, peppermint oil, fennel oil, black cumin oil.

Terpenes, which is a constituent of an essential oil can be isolated from essential oils and are also suitable skin penetration enhancers. Terpenes do not have the aromatic character but contains carbon and hydrogen atoms with or without oxygen. Exemplary terpenes include the following classes along with specific examples in that particular class:

TABLE 1

| Class | Exemplary Terpenes | Source |
|---|---|---|
| ACYCLIC MONOTERPENES (Alcohols) | Geraniol and nerol | Geraniol is an unsaturated primary alcohol found in *geranium* and other essential oils. It is found as esters and as a glucoside, but mainly occurs in the free form. Nerol is the isomeric alcohol and is found in various essential oils, primarily in neroli and bergamot oils Palmarosa oil contains more geraniol than any other oil and for nerol it is |
| | Linalol | Linalol is found as (+)- and (−)-forms in the oil of Linaloe (a plant found in Central America), but can also be found free and as esters in numerous other essential oils. Rosewood oil contains more linalol than any other oil. |

TABLE 1-continued

| Class | Exemplary Terpenes | Source |
|---|---|---|
| MONOCYCLIC MONOTERPENES (Hydrocarbons) | Limonene | The optically active limonene is widespread in nature and is found in its (+)- and (−)- forms in various essential oils such as bergamot, caraway, lemon and orange oils. The signature oils for d-limonene and l-limonene is grapefruit and fleabane, |
| MONOCYCLIC MONOTERPENES (Alcohols) Alcohols related to α-terpineol | α-Terpineol | Found in many essential oils such as camphor, neroli and petitgrain oil. The signature oil is lemon eucalyptus. |
| | β-Terpineol | Isomeric with α-terpineol, but is not isolated from natural sources. Found in commercial terpineol. |
| | γ-Terpineol | Second isomer of α-terpineol and is found in at least one essential oil and commercial terpineol. |
| MONOCYCLIC MONOTERPENES (Alcohols) Alcohols derived from thymol | Menthol | Menthol is a constituent of numerous peppermint oils and is found as its (−)-form. |
| MONOCYCLIC MONOTERPENES (Alcohols) Alcohols derived from carvacrol | Carveol | Carveol is found in caraway oil. |
| MONOCYCLIC MONOTERPENES (Ketones) Ketones related to menthone | Menthone | (−)-form is found in numerous peppermint oils, (+)-form also occurs naturally. |
| | Pulegone | Found in pennyroyal and many other essential oils as its (+)- |
| | iso-Pulegone | Often an accompaniment of pulegone in essential oils. |
| | Piperitone | Occurs in numerous eucalyptus oils as (+)- and (−)-forms. |
| MONOCYCLIC MONOTERPENES (Ketones) Ketones related to carvomenthone | Carvomenthone | Isomeric with menthone and is a saturated ketone. (−)-Form is found in numerous essential oils. |
| | Carvone Unsaturated ketone | Occurs in its (+)-, (−)- and (±)-forms and is the main constituent of caraway and dill oils. It can also be found in spearmint |
| MONOCYCLIC MONOTERPENES (Oxides) | 1,8-Cineole | Widespread in essential oils, particularly in eucalyptus and wormseed oil. |
| BICYCLIC MONOTERPENES (Hydrocarbons) | α-Thujene | Found in numerous essential oils. |
| BICYCLIC MONOTERPENES (Hydrocarbons) | Car-3-ene | Found in several turpentine oils. |
| BICYCLIC MONOTERPENES (Hydrocarbons) | α-Pinene | Widespread in nature, found in most essential oils of Coniferae. It is the main constituent of turpentine oil. Secreted by conifers, turpentine oil consists of resinous material dissolved in |
| | β-Pinene (Nopinene) | Isomeric with α-pinene. Its signature oil is galbanum. |
| BICYCLIC MONOTERPENES (Oxygenated derivatives) | Verbenol, verbenone and verbanone | Verbenol and verbenone has been found in nature, with the latter being found in *verbena* oil. The signature oil for verbenone is rosemary verbenone. |
| BICYCLIC MONOTERPENES (Ketones - camphane group) | Camphor | Not widely distributed in nature, is the major constituent of camphor oil, obtained from the leaves and wood of the camphor tree (*Cinnamomum* |
| BICYCLIC MONOTERPENES (Ketones - fenchane group) | Fenchone | Occurs as the optically active forms in fennel, thuja and cedar leaf oils. |
| SESQUITERPENES (Alcohol) | Farnesol | Widely distributed in flower oils, in particular those of the acacia, cyclamen and the rose. |
| | Nerolidol | Isomeric with farnesol and found in neroli oil. |

TABLE 1-continued

| Class | Exemplary Terpenes | Source |
| --- | --- | --- |
| | (−)-Guaiol | A crystalline alcohol found in guaiacum wood oil. |
| | (+)-Cedrol | Cedarwood oil. |
| | (−)-α-Bisabolol | Camomile oil. |
| SESQUITERPENES (Hydrocarbon) | Bisabolene | Widespread in nature, found in bergamot and myrrh oils. Also in many other essential oils. |
| | The Azulenes (Unsaturated hydrocarbons) | All hydrocarbons are derived from azulene ($C_{10}H_8$), a parent hydrocarbon. Most of those attained from natural origin have the molecular formula $C_{15}H_{18}$. Azulenes is responsible for the blue color of certain essential oils, or when essential oils become blue/violet when undergoing processes which might |
| | (+)-Longifolene | Tricyclic sesquiterpene found in the essential oil of *Pinus longifolia*. |
| | β-Caryophyllene | Main hydrocarbon constituent of clove oil. |
| | (+)-Aromadendrene | Eucalyptus oil. |
| | (+)-β-Cedrene | Cedarwood oil. |
| ACYCLIC DITERPENES (Alcohol) | Phytol | Found in rosemary oil. |
| ACYCLIC TRITERPENES (Hydrocarbon) | Squalene | It is found in the unsaponifiable fraction of shark liver oil and in several plant sources such as vegetable oils and several fungi. Jasmine is the signature oil. |

In some embodiments, the terpene menthol is used as a skin penetration enhancer in a composition containing L-arginine.

Exemplary fixed oils or fatty acids include fish oil, fatty acids from algae and phospholipids (e.g. phosphatidylglyceol, phosphatidylethanolamine, phosphatidylcholine, phosphatidylserine, phosphatidic acid, phosphdtylinositol.

Exemplary polysaccharides (polymer of simple sugars and their derivatives) as skin penetration enhancers include chitosan, aloe vera gel or aloe vera juice.

Other skin penetration enhancers can include methyl salicylate, capsaicin (trans-8-methyl-N-vinilly-6-nonenamide, which is an alkaloid derived from hot chili peppers, belonging from the genus *Capsicum* of the Solanaceae family), vitamin E (α-tocopherol and methyl salicylate (oil of wintergreen or wintergreen oil is an organic ester naturally produced by many species of plants, particularly wintergreens).

Skin penetration enhancers such as terpenes and phospholipids can also be used to prepare vesicles (e.g. liposomes, ivansomes and ethosomes) for transdermal delivery. In other embodiments, essential oils can also be incorporated into patches for transdermal delivery. Exemplary oils can include any of the disclosed essential oils. In some embodiments, the essential oils used in patches include menthol oil patches, lemon grass oil, clove oil, eucalyptus oil or combinations thereof. The transdermal patches used can include matrix, microreservoir, reservoir, adhesive and membrane-matrix hybrid type patches.

In some embodiments, the topical composition may include L-arginine in any suitable form and includes menthol, methyl salicylate, or capsaicin with a base or carrier. In other embodiments, the topical composition includes L-arginine and menthol in a range of about 1 wt % to 16 wt %, about 4 wt % to 12 wt %, or about 6 wt % to 10 wt % based on the total weight of the topical. In still other embodiments, the topical composition includes L-arginine and methyl salicylate in a range of about 1 wt % to 30 wt %, about 5 wt % to 25 wt %, or about 10 wt % to 20 wt % based on the total weight of the topical, base carrier with about 30 wt % of methyl salicylate.

Electrical Stimulation & Related Devices

Like L-arginine, electrostimulation may also facilitate blood vessel dilation which allows lactic acid to dissipate from muscular tissue during exercise or during the recovery phase after exercise. Both L-arginine and electrostimulation may allow the delivery of alternative actives, such as pain relief medication into the deeper tissue because of the vasodilation that it produces. In contrast to electrophoresis which requires actives to be in the ionized state for delivery, L-arginine and electrostimulation may allow non-ionized actives to be absorbed to a greater extent than in their absence.

Electro-stimulation may be done with a conductive pad that is separated into 2 polarity regions. An oscillating pulse voltage ranging from 60 Volts to 1000 Volts is applied to pad electrodes and the signal is then transmitted into the muscle transdermal. This is usually the way it is done.

An advantage of using L-arginine and/or electro stimulation is that it may assist in reducing the amount of topical pain reliever needed to produce the same therapeutic effect and in some cases may even reduce the chance of chemical burns that some topical pain relievers may produce. In some embodiments, the topical composition is applied in combination with electro stimulation. In other embodiment provide a method for dilating blood vessels to thereby allow lactic acid to dissipate from muscular tissue during exercise or during the recovery phase after exercise comprising topically administering an effective amount of a topical composition consisting essentially of L-arginine to a subject in combination with use of a transdermal electrically polarized conductive pad attached to an electro-stimulation power controlled device, wherein the effective amount of L-arginine in combination with an electric field (or current) enhancing skin penetration allows lactic acid to dissipate from muscular tissue during exercise or during the recovery phase after exercise.

Pain Relief Medication and Muscle Relaxers

The disclosed topical compositions may also include pain relief medications. Suitable pain relief medications may include non-narcotic analgesics, NSAIDS, COX-2 inhibitors, narcotic pain medication central analgesics, narcotic analgesics and aspirin, topical analgesics or topical anesthetics as well as combinations of these medications. Exemplary pain relief medications include:

| Non-Narcotic Analgesics | | |
|---|---|---|
| Acetaminophen | | |
| NSAIDs (Non-Steroidal Anti-Inflammatory Drugs) | | |
| Bromfenac | Indomethacin | Naproxen |
| Diclofenac | Ketoprofen | Oxaprozin |
| Diflunisal | Ketorolac | Phenylbutazone |
| Etodolac | Meclofenamate | Piroxicam |
| Fenoprofen | Mefenamic Acid | Sulindac |
| Flurbiprofen | Meloxicam | Tolmetin |
| Ibuprofen | Nabumetone | |
| COX-2 Inhibitors | | |
| Celecoxib | | |
| Narcotic Pain Medications (Painkillers) | | |
| Buprenorphine | Levorphanol | Oxycodone |
| Butorphanol | Meperidine | Oxymorphone |
| Codeine | Methadone | Pentazocine |
| Hydrocodone | Morphine | Propoxyphene |
| Hydromorphone | Nalbuphine | Tapentadol |
| Central Analgesics | | |
| Tramadol | | |
| Tramadol and Acetaminophen | | |
| Combinations | | |
| Butalbital, Acetaminophen, and Caffeine | Acetaminophen and Codeine | Aspirin, Caffeine, and Dihydrocodeine |
| Butalbital, Aspirin, and Caffeine | Dihydrocodeine, Acetaminophen, and Caffeine | Aspirin and Codeine |
| Butalbital, acetaminophen, caffeine, and codeine | Hydrocodone and Acetaminophen | Hydrocodone and Aspirin |
| Hydrocodone and Ibuprofen | Oxycodone and Acetaminophen | Oxycodone and Aspirin |
| Morphine/Naltrexone | Pentazocine and Acetaminophen | Pentazocine and Aspirin |
| Pentazocine/Naloxone | Propoxyphene and Acetaminophen | Propoxyphene, Aspirin, and Caffeine |
| Topical Analgesics | | |
| Capsaicin | | |
| Topical Anesthetics | | |
| Benzocaine | Dibucaine | Lidocaine/Prilocaine |
| Benzocaine/Menthol | Lidocaine | |

The disclosed topical compositions may also include muscle relaxants; suitable muscle relaxant are described below Skeletal Muscle Relaxants:

Suitable muscle relaxants are known to those skilled in the art and may be identified, for example, at internet net sites such as http://www.drugs.com/drug-class/skeletal-muscle-relaxants.html and http://www.md-health.com/Muscle-Relaxers.html Homeopathic and Herbal Preparations Suitable homeopathic and herbal preparations are also known to those skilled in the art and may be identified, for example, at internet net sites such http://www.wisegeek.org/what-are-the-different-types-of-over-the-counter-muscle-relaxant.htm. Homeopathic medications generally are based on the idea that you treat a disorder with the same ingredients that cause it, and this holds true for muscle relaxants. Rather than trying to block nerve signals or change the surface chemistry of damaged tissues, these medications typically look to "treat like with like," intending to stop tension and pain with diluted forms of the very supplements that can cause these problems. Examples include *calcarea phosphorica*, which may be helpful for neck and upper back pain and tension; *kali* carb, which is used to treat lower back pain; and *arnica*, which may help relax overworked muscles.

A number of herbs and plant materials can also be used to form what is basically an all-natural over-the-counter muscle relaxant. Herbs like catnip, valerian, bergamot, licorice, basil and caraway are typically believed to have anti-inflammatory properties, which can help reduce joint swelling. Valerian, a flowering perennial plant, has been used since medieval times to treat neck tension. Other herbs, such as kava root, white willow, horsetail and devil's claw, do better at combating pain. Many of these natural alternatives can be found either combined or in isolation in health or wellness stores, and are commonly sold as teas, capsules, or powders.

Some people also find relief by increasing the vitamin and mineral content of their meals. Proper amounts of calcium and magnesium can often help relieve muscle pain, and magnesium can help repair damaged nerve endings, too. Other important vitamins and minerals that help act as muscle relaxants include silica, potassium, vitamin C and alpha lipoic acid.

OTC Muscle Relaxants for Back Pain

Acetaminophen is a multi-purpose antipyretic medicine that reduces fever and eases pain. Also referred to as paracetamol; acetaminophen has limited side effects and hence can be used safely. However proper guidance is always required and overdose of the drug is often associated with liver disorders, skin and allergic rash along with abdominal pain. However, the action of acetaminophen in management of muscle pains is fairly limited see, for example, http://www.simple-remedies.com/health-tips-3/otc-muscle-relaxants.html. A non-steroidal anti-inflammatory drug or NSAID is another over-the-counter relaxant for muscles.

Natural Muscle Relaxants as Alternate Pain Relief

The various limitations are risks associated with the use of OTC have resulted in a need to identify natural muscle relaxants which can provide sustained pain relief. Here are certain natural products that can be beneficial.

Rosemary oil can alleviate pain from muscle cramps and spasms when mixed in a warm bath. Massaging the affected part with rosemary oil can provide sustained relief. Chamomile Essential Oil is also considered to have similar effect and helps in management of muscle spasms, pain and joint aches.

Herb Catnip has a tranquilizing effect that can help reduce inflamed or swollen joints.

Homeopathic remedies are yet another famous pain relievers with treatments like *Calcarea phosphorica, Arnica* and *Kali* carb. These remedies need to be taken in low dosage and should be repeated over several times in a day.

Milk containing turmeric and honey. Turmeric has strong anti-inflammatory properties while honey helps in reducing inflammatory response. Milk is considered to be a mood food and helps reduce anxiety and irritability associated with the muscular pain. Magnesium and calcium supplements play a pivotal role in reducing muscular pain and muscle spasms.

Topical Formulations

The disclosed L-arginine may be formulated as a topical preparation. Topical formulations include creams, ointments, lotions, gels, foams, sprays and patches (transdermal). Typically, the skin surface on which the disclosed topical composition is applied could be on legs, arms, abdomen, or back as may be convenient to the user.

Suitably, the compositions are administered at least one a day (e.g., one a day, twice a day, three times a day, or the like.) for as long as desired, suitably on the order of days to weeks to months, or longer if desired.

Those skilled in the art will readily determine suitable dosages of the topical compositions to be applied for a variety of the disclosed applications and formulations.

The topical compositions disclosed herein may be packaged in any convenient package depending on the particular formulation. Suitable dispensing or packaging may include, for example, squeezable tubes, sachets, pouches, or single or multiple use containers.

The topical compositions of the present disclosure are suitably used to facilitate blood vessel dilation to allow lactic acid to dissipate from muscular tissue during exercise or during the recovery phase after exercise.

Also disclosed is a method for dilating blood vessels to thereby allow lactic acid to dissipate from muscular tissue during exercise or during the recovery phase after exercise. The method includes applying or delivering the topical composition of L-arginine, base and skin penetration enhancers.

The topical compositions disclosed herein provide the advantages of increasing blood flow, dilating blood vessels to thereby allow lactic acid to dissipate from muscular tissue during exercise or during the recovery phase after exercise and for the ability to deliver the composition more selectively to a specific, desired site.

Some additional non-limiting embodiments are provided below to further exemplify the present disclosure:

1. A topical composition comprising an effective amount of L-arginine with a base or carrier component and skin penetration enhancer, the composition capable of dilating blood vessels to thereby allow lactic acid to dissipate from muscular tissue during exercise or during the recovery phase after exercise.

2. A topical composition consisting essentially of an effective amount of L-arginine with a base or carrier component and skin penetration enhancer, the composition capable of dilating blood vessels to thereby allow lactic acid to dissipate from muscular tissue during exercise or during the recovery phase after exercise.

3. A topical composition consisting essentially of an effective amount of L-arginine with a base or carrier component and skin penetration enhancer and forskolin, the composition capable of dilating blood vessels to thereby allow lactic acid to dissipate from muscular tissue during exercise or during the recovery phase after exercise.

4. A topical composition consisting of an effective amount of L-arginine with a base or carrier component, and skin penetration enhancer, the composition capable of dilating blood vessels to thereby allow lactic acid to dissipate from muscular tissue during exercise or during the recovery phase after exercise.

5. A topical composition consisting of an effective amount of L-arginine with a base or carrier component, forskolin, and skin penetration enhancer, the composition capable of dilating blood vessels to thereby allow lactic acid to dissipate from muscular tissue during exercise or during the recovery phase after exercise.

6. The topical composition as in any one of the preceding embodiments, wherein the L-arginine comprises about 5 wt % to 60 wt %, about 15 wt % to 50 wt %, or about 20 wt % to 40 wt % of the total weigh of the topical composition.

7. The topical composition as in any one of the preceding embodiments, wherein the L-arginine is L-arginine ethyl ester, L-arginine hydrochloride or a free base of L-arginine.

8. The topical composition of embodiments 1-5 wherein the effective amount of forskolin comprises about 0.01-1 wt %, preferably about 0.1-0.5 wt %, or more preferably about 0.1 wt % based on the weight of the topical composition.

9. The topical composition as in any one of the preceding embodiments, wherein the base components comprises from about 30 wt % to 80 wt %, about 40 wt % to 70 wt %, or about 50 wt % to 60 wt % based on the total weight of the topical composition.

10. The topical composition as in any one of the preceding embodiments, wherein the base is selected from oil in water emulsion or water in oil emulsion, anhydrous silicone base, lipophilic foam base, transdermal cream base, or transdermal gel base.

11. The topical composition as in any one of the preceding embodiments, wherein the skin penetration enhancers comprise essential oils, fatty acids, or polysaccharides.

12. The topical composition as in any one of the preceding embodiments, wherein the skin penetration enhancers are selected from methyl salicylate, menthol, *arnica*, capsaicin and hyaluronic acid.

13. The topical composition as in any one of the preceding embodiments, wherein the skin penetration enhancers comprise about 1 wt % to 50 wt %, about 5 wt % to 40 wt %, or about 10 wt % to 35 wt % based on the weight of the topical composition.

14. The topical composition as in any one of the preceding embodiments, wherein the skin penetration enhancers comprise methyl salicylate in a range of about 1 wt % to 30 wt %, about 5 wt % to 25 wt %, or about 10 wt % to 20 wt % based on the total weight of the topical composition.

15. The topical composition as in any one of the preceding embodiments, wherein the skin penetration enhancers comprise menthol in a range of about 1 wt % to 16 wt %, about 4 wt % to 12 wt %, or about 6 wt % to 10 wt % based on the total weight of the topical.

16. The topical composition as in any one of the preceding embodiments, wherein in topical composition is in the form of a gel, cream, ointment, foam, spray or patch.

17. The topical composition as in any one of the preceding embodiments, wherein in topical composition further comprises a pain reliever and/or a muscle relaxant.

18. A method for dilating blood vessels to thereby allow lactic acid to dissipate from muscular tissue during exercise or during the recovery phase after exercise comprising delivering a topical composition to an area of the skin where desired, the topical composition comprising an effective amount of L-arginine with a base or carrier component and skin penetration enhancer.

19. The method of claim 18 or any one of the preceding embodiments, wherein the L-arginine is L-arginine ethyl ester, L-arginine hydrochloride or a free base of L-arginine.

20. The method of claim 18 or any one of the preceding embodiments, wherein the base components comprises about 30 wt % to 80 wt %, about 40 wt % to 70 wt %, or about 50 wt % to 60 wt % based on the total weight of the topical composition.

21. The method of claim 18 or any one of the preceding embodiments, wherein the base is selected from oil in water emulsion or water in oil emulsion, anhydrous silicone base, lipophilic foam base, transdermal cream base.

22. The method of claim 18 or any one of the preceding embodiments, wherein the skin penetration enhancers comprise essential oils, fatty acids, or polysaccharides.

23. The method of claim 18 or any one of the preceding embodiments, wherein the skin penetration enhancers are selected from methyl salicylate, menthol, *arnica*, capsaicin and hyaluronic acid.

24. The method of claim 18 or any one of the preceding embodiments, wherein the skin penetration enhancers comprise about 1 wt % to 50 wt %, about 5 wt % to 40 wt %, or about 10 wt % to 35 wt % based on the weight of the topical composition.

25. The method of claim 18 or any one of the preceding embodiments, wherein the skin penetration enhancers comprise methyl salicylate in a range of about 1 wt % to 30 wt %, about 5 wt % to 25 wt %, or about 10 wt % to 20 wt % based on the total weight of the topical composition.

26. The method of claim 18 or any one of the preceding embodiments, wherein the skin penetration enhancers comprise menthol in a range of about 1 wt % to 16 wt %, about 4 wt % to 12 wt %, or about 6 wt % to 10 wt % based on the total weight of the topical composition.

27. The method of claim 18 or any one of the preceding embodiments, wherein in topical composition is in the form of a gel, cream, ointment, foam, spray or patch.

28. The method of claim 18 or any one of the preceding embodiments, wherein in topical composition further comprises a pain reliever and/or a muscle relaxant.

29. A method for dilating blood vessels to thereby allow lactic acid to dissipate from muscular tissue during exercise or during the recovery phase after exercise comprising topically administering an effective amount of a topical composition consisting essentially of L-arginine to a subject in combination with use of a transdermal electrically polarized conductive pad attached to an electro-stimulation power controlled device, wherein the effective amount of L-arginine in combination with an electric field (or current) enhancing skin penetration allows lactic acid to dissipate from muscular tissue during exercise or during the recovery phase after exercise.

It will be readily apparent to one of ordinary skill in the relevant arts that other suitable modifications and adaptations to the composition, methods and applications described herein can be made without departing from the scope of any of the embodiments. The following examples are included herewith for purposes of illustration only and are not intended to be limiting.

EXAMPLES

A topical composition as an oil in water emulsion is formulated with L-arginine monohydrochloride 20 wt %, with or without forskolin 0.1% wt %, methyl salicylate 15 wt %, menthol 5 wt %, and oil in water (O/W) emulsion with preservative 60 wt %. This composition is packaged in 5 mL foil package. After exercise, this topical composition is applied to skin to dilate blood vessels allowing lactic acid to dissipate from muscular tissue.

The invention claimed is:

1. A topical composition comprising about 20-40 wt % L-arginine, about 0.01-1 wt % forskolin, about 10-35 wt % skin penetration enhancer consisting of a mixture of methyl salicylate and menthol, and about 40-70 wt % base or carrier component, the composition dilating blood vessels to thereby allow lactic acid to dissipate from muscular tissue during exercise or during the recovery phase after exercise.

2. The topical composition of claim 1, wherein the L-arginine is L-arginine ethyl ester, L-arginine hydrochloride or a free base of L-arginine.

3. The topical composition of claim 1, wherein the base is selected from oil in water emulsion or water in oil emulsion, anhydrous silicone base, lipophilic foam base, transdermal cream base, or transdermal gel base.

4. The topical composition of claim 1, wherein methyl salicylate is in a range of about 10 wt % to 20 wt % based on the total weight of the topical composition.

5. The topical composition of claim 1, wherein the topical composition is in the form of a gel, cream, ointment, foam, spray or patch.

6. The topical composition of claim 1, wherein the topical composition further comprises a pain reliever and/or a muscle relaxant.

7. The topical composition of claim 1, wherein the 10-35 wt % skin penetration enhancer consisting of a mixture of methyl salicylate and menthol consists of about 1-16 wt % menthol with the remainder consisting of methyl salicylate.

* * * * *